United States Patent [19]

Scholz

[11] 4,180,523
[45] Dec. 25, 1979

[54] MANUFACTURE OF N-[3,4-DIMETHYLPHENYL]-D-RIBAMINE

[75] Inventor: Herbert Scholz, Ludwigshafen, Fed. Rep. of Germany

[73] Assignee: BASF Aktiengesellschaft, Fed. Rep. of Germany

[21] Appl. No.: 923,537

[22] Filed: Jul. 11, 1978

Related U.S. Application Data

[63] Continuation of Ser. No. 745,433, Nov. 26, 1976, abandoned.

[30] Foreign Application Priority Data

Dec. 24, 1975 [DE] Fed. Rep. of Germany ....... 2558515
Dec. 24, 1975 [DE] Fed. Rep. of Germany ....... 2558516

[51] Int. Cl.$^2$ .............................................. C07C 91/40
[52] U.S. Cl. ........................................ 260/573; 536/53
[58] Field of Search ........................... 536/53; 260/573

[56] References Cited

U.S. PATENT DOCUMENTS

| | | | |
|---|---|---|---|
| 2,193,433 | 3/1940 | Salzberg | 260/573 X |
| 2,411,611 | 11/1946 | Bergel et al. | 536/53 |
| 2,422,997 | 6/1947 | Wuest | 536/18 |
| 4,026,944 | 5/1977 | Bohm | 260/580 |

FOREIGN PATENT DOCUMENTS

1342020  12/1973  United Kingdom ................... 260/573

OTHER PUBLICATIONS

Adams, "Organic Reactions", vol. 8, p. 7 (1954).

*Primary Examiner*—John Doll
*Attorney, Agent, or Firm*—Keil & Witherspoon

[57] ABSTRACT

A process for the manufacture of N-[3,4-dimethylphenyl]-D-ribamine, in which (a) a mixture of 3,4-dimethylaniline and/or 3,4-dimethylnitrobenzene and a D-ribonic acid derivative of the formula

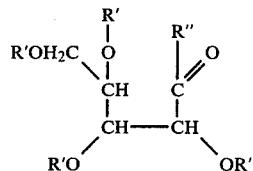

where each R' is hydrogen or one of the R's together with R" is a single bond, R" is hydroxyl, R''' —O— or, together with R', a single bond, and R''' is a hydrocarbon radical of 1 to 10 carbon atoms which may or may not be substituted by hydroxyl groups, or (b) D-ribonic acid 3,4-dimethylanilide is catalytically hydrogenated in an inert solvent at from above 100° C. to 155° C.

5 Claims, No Drawings

MANUFACTURE OF N-[3,4-DIMETHYLPHENYL]-D-RIBAMINE

This is a continuation of application Ser. No. 745,433, filed Nov. 26, 1976, which application has now been abandoned.

The present invention relates to a new process for the manufacture of N-[3,4-dimethylphenyl]-D-ribamine of the formula I

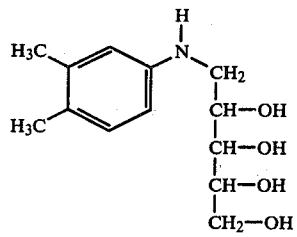

N-[3,4-Dimethylphenyl]-D-ribamine, an important intermediate for the manufacture of vitamin B2, may be manufactured, for example in accordance with a process disclosed in U.S. Pat. No. 2,384,105, by reacting D-ribose and 3,4-dimethylaniline and catalytically hydrogenating the product at up to 100° C. Since D-ribose is difficult to obtain, U.S. Pat. No. 2,411,611 provides a process in which 3,4-dimethylaniline is condensed with D-ribonic acid γ-lactone to give D-ribonic acid 3,4-dimethylanilide, from which latter compound N-[3,4-dimethylphenyl]-D-ribamine is then produced by acetylating, chlorinating, hydrogenating and desacetylating. This involved process does not permit economical manufacture of N-[3,4-dimethylphenyl]-D-ribamine.

It has also already been proposed to hydrogenate a mixture of 3,4-dimethylaniline or the corresponding nitro compound and D-ribonic acid γ-lactone in an inert solvent, using platinum oxide. In this process, disclosed in U.S. Pat. No. 2,422,997, which is carried out at below 100° C. to avoid side-reactions, N-[3,4-dimethylphenyl]-D-ribamine is obtained in moderate yields.

It is an object of the present invention to provide a process for the manufacture of N-[3,4-dimethylphenyl]-D-ribamine which permits manufacture of this important vitamin intermediate by a very simple method, and in good yield and high purity.

I have found that this object is achieved and that N-[3,4-dimethylphenyl]-D-ribamine of the formula I can be manufactured advantageously when (a) a mixture of 3,4-dimethylaniline and/or 3,4-dimethylnitrobenzene and a D-ribonic acid derivative of the formula II

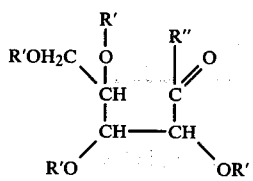

where each R' is hydrogen or one of the R's together with R" is a single bond, R" is hydroxyl, R''' —O— or, together with R', a single bond, and R''' is a hydrocarbon radical of 1 to 10 carbon atoms which may or may not be substituted by hydroxyl groups, or (b) D-ribonic acid 3,4-dimethylanilide of the formula III

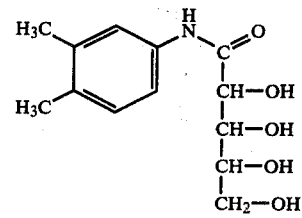

is catalytically hydrogenated in an inert solvent at from above 100° C. to 155° C.

Suitable starting compounds of the formula II are lactones of D-ribonic acid, D-ribonic acid itself or esters thereof. The alcohol radicals R''' may be straight-chain or branched, saturated or unsaturated hydrocarbon radicals of 1 to 10, preferably of 1 to 5, carbon atoms, which may or may not be substituted by hydroxyl groups. Examples of radicals R''' are alkyl, e.g. methyl or butyl. D-Ribonic acid γ-lactone is the preferred starting compound.

D-Ribonic acid 3,4-dimethylanilide of the formula III, to be used as a starting compound, is readily obtainable, for example by known methods, by reacting D-ribonic acid γ-lactone with 3,4-dimethylaniline (J. Org. Chem. 166 (1945)).

Suitable inert solvents are conventional organic solvents which undergo no significant change, or no change at all, under the reaction conditions. Examples are alcohols, e.g. methanol, ethanol, propanol and butanol, or ethers, e.g. dioxane, the last-mentioned being the preferred solvent.

Suitable catalysts for the catalytic hydrogenation are, for example, transition element metals, e.g. copper, chromium, nickel, iron, platinum, palladium, rhodium, cerium, thorium and zinc, as well as aluminum and magnesium metals or the oxides of the said metals. Mixtures of the above metals or metal oxides, such as the mixed oxides mentioned in Schwab: "Handbuch der Katalyse", volume 5, pages 567–577, are also very suitable. Catalysts containing copper oxide and/or copper, especially those containing finely divided copper oxide and/or copper on a catalyst carrier, have proved particularly advantageous. Examples of carriers present in such catalysts are refractory oxides, e.g. chromium oxide, aluminum oxide or cerium oxide. Such catalysts are described, for example, by H. Adkins in Organic Reactions, volume VIII, 1954, pages 8 and 9, and in German Laid-Open Application DOS No. 2,024,282. Amongst these catalysts, those containing copper oxide and chromium oxide, and those containing copper oxide and aluminum oxide, are very suitable.

It is particularly advantageous to treat the catalysts with hydrogen before they are used. This prehydrogenation is effected, for example, at up to 400° C., preferably at from 150° to 250° C., under a hydrogen pressure of from 0.01 to 300 bars.

The hydrogenation according to the invention is carried out at from above 100° to 155° C., preferably at from 125° to 145° C. The hydrogen pressure is from 1 to 1,000 bars, preferably from 100 to 300 bars. The starting materials are advantageously reacted in the stoichiometric ratio. It is advantageous to use from 100 to 400 parts by weight of solvent, based on 100 parts by weight of the mixture of starting materials.

The process of the invention gives pure N-[3,4-dimethylphenyl]-D-ribamine in good yield. This advantageous outcome is surprising, since it had previously been assumed that hydrogenation of a mixture of 3,4-dimethylaniline and D-ribonic acid γ-lactone at above 100° C. did not give any N-[3,4-dimethylphenyl]-D-ribamine (J. Amer. Chem. Soc. 68, (1946) 1,777). In addition, epimerization, with formation of D-arabonic acid 3,4-dimethylanilide had to be feared (J. Chem. Soc. 165 (1945)).

EXAMPLE 1

A solution of 29.6 g (0.2 mole) of D-ribonic acid γ-lactone and 24.2 g (0.2 mole) of 3,4-dimethylaniline in 150 ml of dioxane is thoroughly mixed with 18 g of pre-hydrogenated copper oxide/chromium oxide catalyst, containing barium, and hydrogenated, in a hydrogenation autoclave, at 135° C. under a hydrogen pressure of 250 bars for 32 hours. After the hydrogenation has ended and the mixture has been cooled, 250 ml of ethanol are added and the batch is heated to dissolve the N-[3,4-dimethylphenyl]-D-ribamine which has partially precipitated. The catalyst is filtered off, the filtrate is concentrated and the residue is recrystallized from ethanol. Yield: 62% of N-[3,4-dimethylphenyl]-D-ribamine.

Melting point: 137° C.; $[\alpha]_D = -21.94°$ (C=0.4; methanol)

| Analysis: $C_{13}H_{21}NO_4$ Molecular weight = 255.31 | | | | |
|---|---|---|---|---|
| | % C | % H | % O | % N |
| found: | 61.2 | 8.1 | 25.4 | 5.5 |
| calculated: | 61.15 | 8.29 | 25.07 | 5.49 |

$^{13}$C NMR-spectrum (DDMSO; TMS standard)

Chemical shift (ppm): 147.2; 136.1; 129.8; 122.9; 114.2; 110.0; 73.5; 72.8; 70.4; 63.3; 46.2; 19.6; 18.3.

In order to pre-hydrogenate the catalyst, 18 g of copper oxide/chromium oxide catalyst in 150 ml of dioxane are treated, at 200° C., with hydrogen under a pressure of 200 bars for 1 hour, with good mixing.

The copper oxide/chromium oxide catalyst pre-hydrogenated in this way is introduced into the hydrogenation autoclave whilst excluding air, and is immediately employed for the hydrogenation.

The procedure employed in the Examples which follow is as described in Example 1. For this reason, only differences from the procedure described are mentioned.

EXAMPLE 2

Catalyst: 18 g of a pre-reduced copper oxide/aluminum oxide catalyst which has been obtained by heating a compound having the composition $Cu_6Al_2(CO_3)(OH)_{16} \cdot 4H_2O$.

Time: 9 hours
Yield: 72%
Melting point: 138° C.

The IR spectrum, $^{13}$C NMR-spectrum and analysis confirm the structure of N-[3,4-dimethylphenyl]-D-ribamine.

$[\alpha]_D = -22.3°$ (C=0.41; methanol).

The catalyst is pre-hydrogenated by passing a stream of hydrogen over 18 g of copper oxide/aluminum oxide catalyst for 12 hours in an oven at 200° C.

EXAMPLE 3

Temperature: 140° C.
Yield: 56%
Melting point: 136° C.

EXAMPLE 4

Temperature: 130° C.
Yield: 71%
Melting point: 140° C.
$[\alpha]_D = 22.4°$ (C=0.39; methanol)

EXAMPLE 5

Instead of 3,4-dimethylaniline, 0.2 mole of 3,4-dimethylnitrobenzene is employed.

Hydrogenation: 24 hours at room temperature under 80 bars hydrogen pressure, followed by 15 hours at 140° C. under 240 bars hydrogen pressure.

The yield of N-[3,4-dimethylpentyl]-D-ribamine is somewhat lower than in Example 1.

EXAMPLE 6

12 g of pre-hydrogenated copper oxide/chromium oxide catalyst.
Yield: 59%.

EXAMPLE 7

Solvent used for the hydrogenation: methanol.
The yield is somewhat lower than in Example 1.

EXAMPLE 8

Batch: 44.4 g (0.3 mole) of D-ribonic acid γ-lactone and 24.2 g (0.2 mole) of 3,4-dimethylaniline.
15 hours hydrogenation at 300 bars $H_2$ and 135° C.
Yield: 60%.

EXAMPLE 9

18 g of copper oxide/chromium oxide catalyst are pre-hydrogenated for 1 hour in 150 ml of dioxane at 200° C. under 200 bars hydrogen pressure. 53.9 g (0.2 mole) of D-ribonic acid 3,4-dimethylanilide are hydrogenated with the fresh pre-hydrogenated copper oxide/chromium oxide catalyst for 36 hours at 135° C. under 300 bars hydrogen pressure, with good mixing. The catalyst is filtered off, the filtrate is concentrated and the residue is recrystallized from ethanol.

Yield: 50% of N-[3,4-dimethylphenyl]-D-ribamine.
Melting point: 138° C.; $[\alpha]_D = -21.8°$ C. (C=0.4; methanol)

| Analysis: $C_{13}H_{21}NO_4$ Molecular weight = 255.31 | | | | |
|---|---|---|---|---|
| | % C | % H | % O | % N |
| found: | 61.2 | 8.1 | 25.4 | 5.5 |
| calculated: | 61.15 | 8.29 | 25.07 | 5.49 |

$^{13}$C NMR-spectrum (DDMSO; TMS standard)

Chemical shift (ppm): 147.2; 136.1; 129.8; 122.9; 114.2; 110.0; 73.5; 72.8; 70.4; 63.3; 46.2; 19.6; 18.3.

The IR spectrum proves the structure of N-[3,4-dimethylphenyl]-D-ribamine.

I claim:

1. A process for the manufacture of N-[3,4-dimethylphenyl]-D-ribamine of the formula I

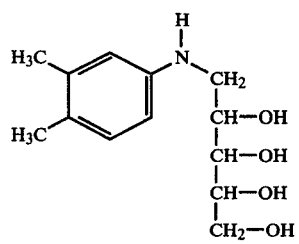

which comprises: catalytically hydrogenating 3,4-dimethylaniline or 3,4-dimethylnitrobenzene and a D-ribonic acid derivative of the formula II

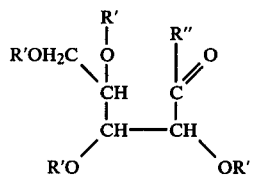

where each R' is hydrogen or one of the R's together with R" is a single bond, R" is hydroxyl, OR"' or, together with R', a single bond, and R"' is a hydrocarbon radical of 1 to 10 carbon atoms which may or may not be substituted by one or more hydroxyl groups in an inert solvent at from 125° C. to 155° C. using an effective amount of catalyst which contains copper oxide, copper or mixtures thereof.

2. A process for the manufacture of N-[3,4-dimethylphenyl]-D-ribamine of the formula I

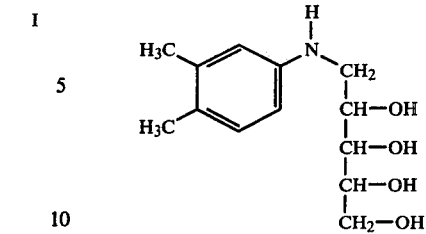

which comprises: catalytically hydrogenating D-ribonic acid 3,4-dimethylanilide of the formula III

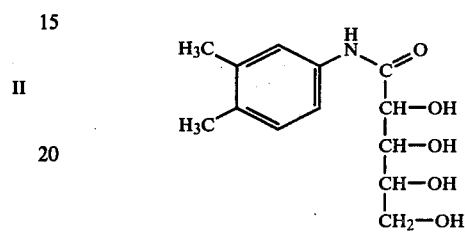

in an inert solvent at from 125° C. to 155° C. using an effective amount of catalyst which contains copper oxide, copper or mixtures thereof.

3. A process as set forth in claim 1, wherein 3,4-dimethylaniline or 3,4-dimethylnitrobenzene with D-ribonic acid γ-lactone as the D-ribonic acid derivative, is catalytically hydrogenated.

4. A process as set forth in claim 1, wherein the temperature is from 125° to 145° C.

5. A process as set forth in claim 2, wherein the temperature is from 125° to 145° C.

* * * * *